US007262066B2

(12) United States Patent
McNamara et al.

(10) Patent No.: US 7,262,066 B2
(45) Date of Patent: Aug. 28, 2007

(54) SYSTEMS AND METHODS FOR THIN FILM THERMAL DIAGNOSTICS WITH SCANNING THERMAL MICROSTRUCTURES

(75) Inventors: Shamus McNamara, Louisville, KY (US); Yogesh B. Gianchandani, Ann Arbor, MI (US)

(73) Assignee: PicoCal, Inc., Ypsilanti, MI (US)

( * ) Notice: Subject to any disclaimer, the term of this patent is extended or adjusted under 35 U.S.C. 154(b) by 1 day.

(21) Appl. No.: 11/219,141

(22) Filed: Sep. 1, 2005

(65) Prior Publication Data

US 2006/0051884 A1   Mar. 9, 2006

Related U.S. Application Data

(60) Provisional application No. 60/607,331, filed on Sep. 3, 2004.

(51) Int. Cl.
*H01L 21/66* (2006.01)
(52) U.S. Cl. ................... 438/14; 257/E21.135
(58) Field of Classification Search .............. 438/6, 438/10, 104, 107–114, 118, 121–123, 128–129, 438/135, 142, 145, 149, 151, 157, 176, 484, 438/184, 193, 195–198, 200–211, 218, 237, 438/165, 248, 268, 343, 308, 337, 353
See application file for complete search history.

(56) References Cited

U.S. PATENT DOCUMENTS

| 5,246,782 | A  | * | 9/1993 | Kennedy et al. | ............. 428/421 |
| 6,996,147 | B2 | * | 2/2006 | Majumdar et al. | ........ 372/43.01 |
| 6,998,278 | B2 | * | 2/2006 | Silverbrook | .................. 438/21 |
| 2002/0011852 | A1 | * | 1/2002 | Mandelis et al. | ............ 324/752 |
| 2005/0214956 | A1 | * | 9/2005 | Li et al. | ....................... 438/14 |

* cited by examiner

*Primary Examiner*—Michael Lebentritt
*Assistant Examiner*—Andre' Stevenson
(74) *Attorney, Agent, or Firm*—Perkins Coie LLP

(57) ABSTRACT

Systems and methods are described for identifying characteristics and defects in material such as semiconductors. Methods include scanning a thermal probe in the vicinity of a semiconductor sample, applying stimuli to the thermal probe, and monitoring the interaction of the thermal probe and the semiconductor. The stimulus can be applied by a variety of methods, including Joule heating of a resistor in the proximity of the probe tip, or optically heating a tip of the thermal probe using a laser. Applications of the invention include identification of voids in metallic layers in semiconductors; mapping dopant concentration in semiconductors; measuring thickness of a sample material; mapping thermal hot spots and other characteristics of a sample material.

34 Claims, 8 Drawing Sheets

SYSTEMS AND METHODS FOR THIN FILM THERMAL DIAGNOSTICS WITH SCANNING THERMAL MICROSTRUCTURES

CLAIM OF PRIORITY

This application claims the benefit of U.S. Application No. 60/607,331 filed Sep. 3, 2004, which is incorporated herein in its entirety by reference.

BACKGROUND

1. Field of the Invention

The invention relates to the testing and manufacturing of thin film materials. More specifically, the invention relates to thermal diagnostics for finding defects and/or measuring or identifying features of integrated circuits.

2. Background of the Invention

A variety of scanning thermal probes have been developed for mapping spatial variations in surface temperatures or the thermal properties of samples. The transducing elements for such devices have included thermocouples, Schottky diodes, bolometer-type resistance change devices, and bimorphs. A bolometer-type sensing element, which maps temperature by fractional changes in electrical resistance, has certain advantages for microcalorimetry applications. In particular, the resistor in the probe can be used to supply heat if sufficient current is passed through it. Because the tip temperature is ultimately influenced by the heat flow between the tip and the sample, variations in thermal conductance across the sample can be mapped by such a probe. If the heat is supplied by a periodic signal, local variations in thermal capacity can also be measured. In essence, because the probe tip serves as a point source of heat as well as a temperature sensor, such devices can be used as a spatially localized microcalorimeter. See A. Hammiche, et al., J. Vac. Sci. Technol. B, Vol. 14, 1996, pp. 1486, et seq.; L. E. Ocola, et al., Apl. Phys. Lett., Vol. 68, 1996, pp. 717, et seq.; D. Fryer, et al., Proc. SPIE, Vol. 333, 1998, pp. 1031, et seq.

While microcalorimetry techniques that use thermal probes for characterization of materials have been reported, they have failed to anticipate recent developments in both probe technology and rapidly evolving application areas. For example, past efforts in using thermally sensitive probes for microcalorimetry were focused on single point measurements that were made with either wire-based probes that were fabricated by non-lithographic means, or on lithographically micromachined single probes that were not appropriate for high-throughput measurements. In recent years, efforts at developing thermal probes using polyimide as the structural material have led to highly compliant devices that can be operated in contact with the sample surface without force feedback, even for relatively soft samples. In addition, the use of lithographic fabrication methods has permitted the integration of more sophisticated functionality than afforded by a single thermal sensor, and the development of more complex structures than a single cantilever or loop. In general, the thermal, mechanical, and electrical properties of the scanning microstructures can all be optimized for the particular application at hand. This evolution in microstructure technology has also opened up the possibility of using new sensing methods. For example, it is possible to stimulate a sample using one part or element of a probe-like microstructure, while the sensing is performed by a different part in the same structure or potentially even a separate microstructure that is coupled to the first in a pre-determined manner. As a further example, the nature of the electrical and thermal waveforms that may be used with these structures is more diverse than the time-invariant (fixed value) and the oscillatory waveforms that have been anticipated in the past. Thus, impulse-type waveforms that are not periodic may be used to determine the properties of a pixel or the simultaneous characterization of multiple disparate pixels. More complex waveforms are also anticipated. In addition, the potential application arenas for these systems have also changed. Several emerging needs for scanning thermal diagnostics in the semiconductor industry have not been anticipated or addressed in the past. These applications, which typically require high speed mapping of relatively large areas, and may sometimes require only qualitative comparisons, potentially include: the detection of spatially distributed defects in thin films such as sub-surface voids in interconnect metal or defects in the bond interface between two structures or materials; the characterization of process steps such as mapping the distribution of implanted dopant concentration or thickness variation in deposited films; and the correlation and comparison of simultaneously acquired high resolution images of temperature in an operating circuit or the observation of their temporal changes to predict or diagnose reliability. These various shortcomings in existing and previously anticipated know-how are addressed by the systems and methods that are described in this document.

The measurement of sub-surface areas with high speed, high spatial resolution and in a non-destructive manner is a significant challenge in semiconductor process monitoring. Voids in semiconductor surfaces arise to non-idealities in the deposition process. For example, voids may occur in thin film copper interconnects due to non-uniformities in deposition rates related to variations in topography or the proximity and size of features. It is not always possible to detect these defects before the completion of the manufacturing process, and they can potentially make their way into the final device or system, leading to long term reliability problems that are very expensive to detect and correct. Present options for detecting these defects include systems using: laser-induced surface acoustic waves, which have a resolution that exceeds 10 microns and so can only determine large clusters of defects; acoustic microscopy, which offers better resolution but can require the sample to be immersed in a liquid; point-by-point electrical testing, which lacks the necessary throughput to be practical in a production setting; and scanning electron microscopy, which requires the sample to be sectioned, and is accordingly both slow and destructive. These and other inadequacies of the prior art are addressed by this invention.

Dopant mapping in semiconductors is commonly performed by measuring the change in reflectance when the semiconductor is heated with a laser. For a given laser power output, the final temperature of the semiconductor depends upon the thermal conductivity, which corresponds to the dopant concentration. See A. Rosencwaig, Thermal Wave Characterization and Inspection of Semiconductor Materials and Devices, Ch. 5 in Photoacoustic and Thermal Wave Phenomena in Semiconductors, ed. by A. Mandelis (Elsevier Science Publishing, New York, 1987). Systems and methods based on scanning thermal microstructures potentially provide high resolution non-destructive alternatives to existing approaches and may even be used as complementary methods.

The thickness of a thin film on a substrate may be measured using photoacoustic methods. In this procedure, the sample is enclosed within a sealed container and illuminated with a laser through a variable speed optical chopper. The sample is heated by the chopped laser signal, causing the surrounding air to heat. The resulting increase in air pressure is measured. By varying the chopper frequency, the thickness of the thin film may be determined. See D. Almond, Photothermal science and techniques (Chapman and Hall, London) 1996. For this application as well, scanning thermal microstructures potentially provide high resolution non-destructive alternatives to existing approaches.

SUMMARY OF THE INVENTION

The invention includes systems and methods for scanning a thermal probe in the vicinity of a sample material, such as a semiconductor material, applying stimuli to a thermal probe in proximity to the sample, and monitoring the interaction of the thermal probe and the sample. The stimulus can be applied by a variety of methods, including Joule heating of a resistor in the proximity of the probe tip, or optically heating a tip of the thermal probe using a laser. In embodiments of the invention, the interaction may be detected by measuring the time-dependent voltage and current through a resistor in the proximity of the probe tip, whose properties vary depending upon the stimulus applied and the interaction of the probe with the sample.

Defects in integrated circuits may be identified by observing the heat flow from a tip of the probe to the integrated circuit. A defect can cause a different rate of heat flow by impeding or aiding in the heat transport through the integrated circuit. Furthermore, defects can affect the transient heat flow from the probe to the integrated circuit by altering the effective specific heat of the integrated circuit. In embodiments of the invention, voids may be detected within copper interconnects within integrated circuits. In some such embodiments, these voids may be detected by a higher heat flow rate observed initially after a thermal stimulus is applied, or from a lower heat flow rate observed after some time.

Embodiments of the invention may be used to identify the number of dopant atoms in the semiconductor after steps such as ion implantation. In some such embodiments, the number of dopant atoms may be found from the dependence of dopant atom concentration versus heat flow rate. The higher the dopant atom concentration, the lower the heat flow rate in a semiconductor such as silicon.

By applying a periodic thermal stimulus to the top of a thin film on sample material, such as an integrated circuit, embodiments of the invention may be used to measure the thickness of a film. In some embodiments, the interaction between the thermal probe and the sample depends upon the thickness of the thin film, permitting the thickness to be measured through a response of such interaction.

Embodiments of the invention may identify the localized temperature of an integrated circuit; such temperatures may be indicative of the performance of the integrated circuit. A locally hot region ("hot spot") on an integrated circuit may be indicative of a point that has failed or is likely to fail. Embodiments of the invention use a bolometer in the vicinity of the probe tip and apply a brief stimulus to the bolometer to permit a localized temperature measurement to be performed. In some such embodiments, the stimulus may subsequently removed to minimize self-heating of the thermal probe, and allow the temperature of the bolometer to reach equilibrium with the sample before another measurement is performed.

These and other objects of the present invention are described in greater detail in the detailed description of the invention, the appended drawings, and the attached claims.

DETAILED DESCRIPTION OF THE INVENTION

A. Introduction

The invention pertains to the application of a stimulus to a scanning thermal probe and the detection of the thermal interaction between the probe and a sample.

Embodiments of the Invention may Involve the use of One or More of the Following Techniques:

(a) Observation of the frequency response of probes in proximity to the sample. The relevant observables may include one or more of the following: the difference in phase between the applied stimulus and response, the frequencies of the maxima and minima of the phase difference, the amplitude degradation with frequency, and/or the step response.

(b) Observation of the DC response of probes in proximity of the sample.

(c) Application of a periodic sampling algorithm, whereby a stimulus is applied to a thermal probe for a duration of time smaller than the thermal time constant of the probe, thereby minimizing heating of the thermal probe. In embodiments of the invention, this sampling algorithm may be used in conjunction with multiple probes connected to a single interface circuit through a multiplexer.

In some embodiments, one or more of these techniques may be applied simultaneously. Furthermore, the invention also pertains to methods of using the scanning thermal probe to sense thermal properties and events within a sample without the use of a stimulus.

B. Implementation of Thermal Probes

In embodiments of the invention, the thermal probe used in diagnoses of a material sample may be stimulated electrically or with a light source, such as a laser. The thermal probe then induces an effect on the sample, such as adding heat to the sample, heating the sample to a set temperature, introducing an evanescent wave, or introducing a thermo-acoustic wave; other effects that may be induced on the sample shall be apparent to those skilled in the art. The effects of this interaction on the thermal probe are subsequently measured.

The thermal probe can be biased at a temperature and a sinusoidal (or other periodic waveform) applied to the thermal probe. In embodiments of the invention, the temperature of the probe may be measured; alternatively a heat flow which maintains the probe at a constant temperature may be measured. As the frequency is swept, the amplitude or phase is measured. The rate of amplitude roll-off, the phase difference, or the location of the phase maxima and minima may be used to discern properties of the sample.

In embodiments of the invention, a step in temperature or heat flow may be applied to the thermal probe and the time response of the thermal probe may be measured. In alternative embodiments, a constant temperature or constant heat flow may be applied to the thermal probe and the interaction between the thermal probe and the sample may be measured in response.

In embodiments of the invention, the thermal probe may be passively coupled to the sample and the probe temperature measured in response. Such embodiments allow the probe to be used to measure the localized temperature of the sample, heat flow from another portion of the sample, or a thermal wave from another portion of the sample.

In embodiments of the invention, the thermal probe may be stimulated for a very brief duration of time. If the duration is smaller than the thermal time constant of the thermal probe, the temperature of the thermal probe will not be significantly affected. This feature can be used to send a large current pulse through the probe, measure the voltage drop, and thus determine the probe resistance without significant heating occurring.

In embodiments of the invention, defects in a sample, such as an integrated circuit, are found by scanning the probe across the sample and measuring the thermal conductance or thermal capacitance as a function of position. A defect will be manifested as a region with a different thermal conductance or thermal capacitance from that which was expected. The presence of the defect can be deduced by observing the difference in thermal conductance or thermal capacitance between a reference region of the sample and the region with the defect; alternatively the defect can be found by observing a different thermal conductance or thermal capacitance in comparison to a "golden standard," i.e., a sample that is known to be free of defects.

Figure 1:
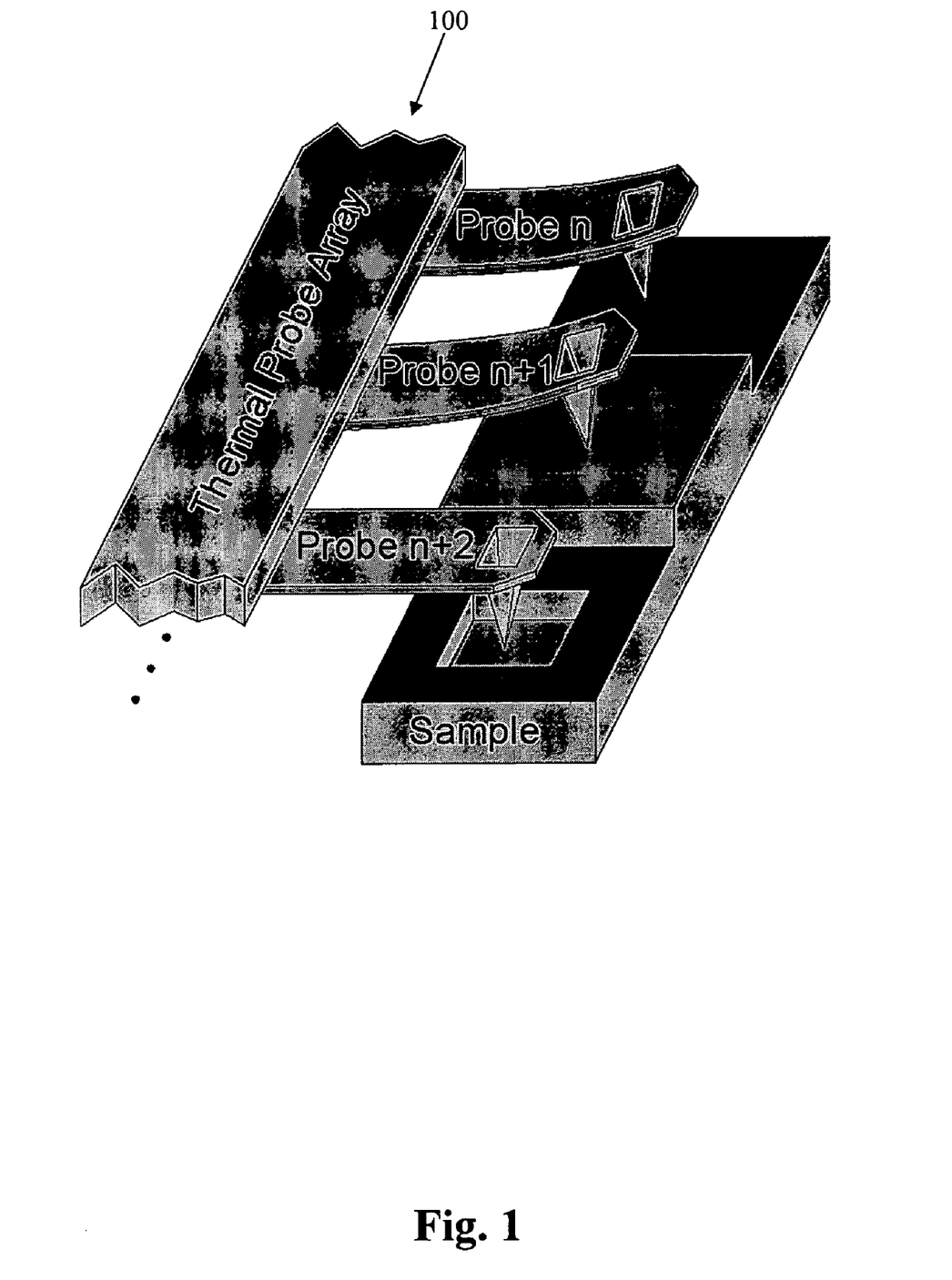
FIG. 1 is a schematic of a thermal probe, in accordance with embodiments of the invention.

A thermal probe used by embodiments of the invention is illustrated in FIG. 1. A sensor is located at the end of a cantilever. The thermal probe, or an array of probes, is scanned across a sample, in a manner similar to an atomic force microscope (AFM). At every location of interest, the electrical properties of the thermal probe are measured, representative of the interaction between the sample and thermal probe as a non-limiting embodiment. One mode of operation is to scan the thermal probe over an area to obtain an image of the area of interest on the sample. A second method is to scan the thermal probe in a line, crossing features of interest. A third method is to move the thermal probe to a single or multiple locations of interest and perform a detailed analysis at those locations.

Figure 2A:
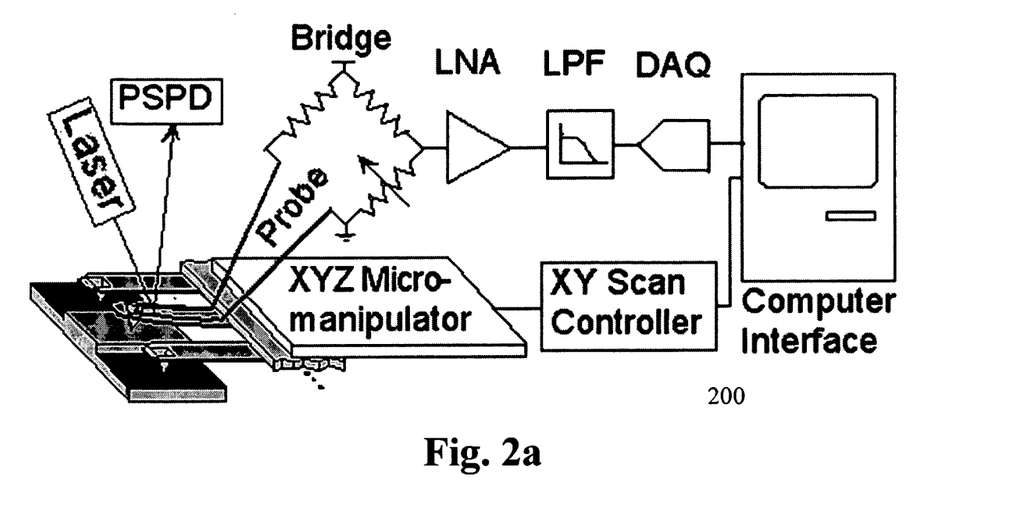
FIG. 2A-B shows schematic diagrams of the components of two exemplary scanning probe microscopes, one with and one without a mechanical z-axis feedback loop, in accordance with embodiments of the invention.
Figure 2B:
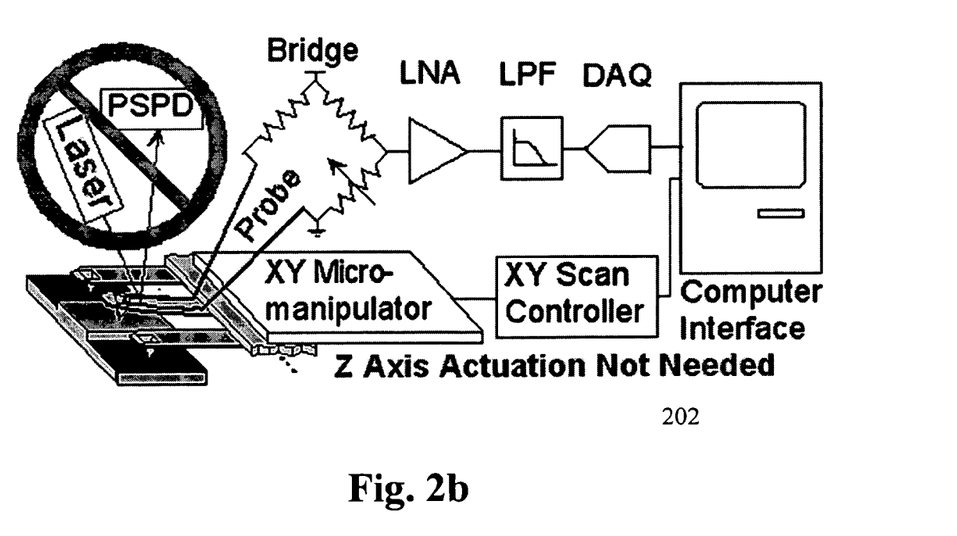

FIGS. 2A and 2B schematically illustrate embodiments of the invention with and without Z-axis feedback, respectively. Z-axis feedback 200 provides the ability to maintain a constant force between the probe and sample, thereby lowering the noise level. But operation without z-axis feedback 202 permits lower cost and a much easier implementation of an array of thermal probes. Embodiments of the invention employ control to maintain proper contact between the probe and sample flexible cantilever that allows the choice of whether to use z-axis feedback.

In some embodiments of the invention, a temperature sensor such as a thermocouple or a bolometer is located at the thermal probe tip. The thermocouple is well suited for applications where the probe tip is not thermally biased and temperature is measured. The bolometer is well suited for applications where the probe tip must be heated to a desired temperature and the heat transfer from probe tip to sample is monitored.

C. Examples of the Application of Thermal Probe

Some of the applications of these methods include (a) finding defects on integrated circuits, such as mapping voids in copper interconnects and mapping damage due to ion implantation (b) mapping the quantity of dopant atoms in a semiconductor, (c) finding the thickness of thin films, and (d) mapping the temperature of an integrated circuit. These applications are further described herein, and other applications of the techniques described herein shall be readily apparent to those skilled in the art.

Figure 3:
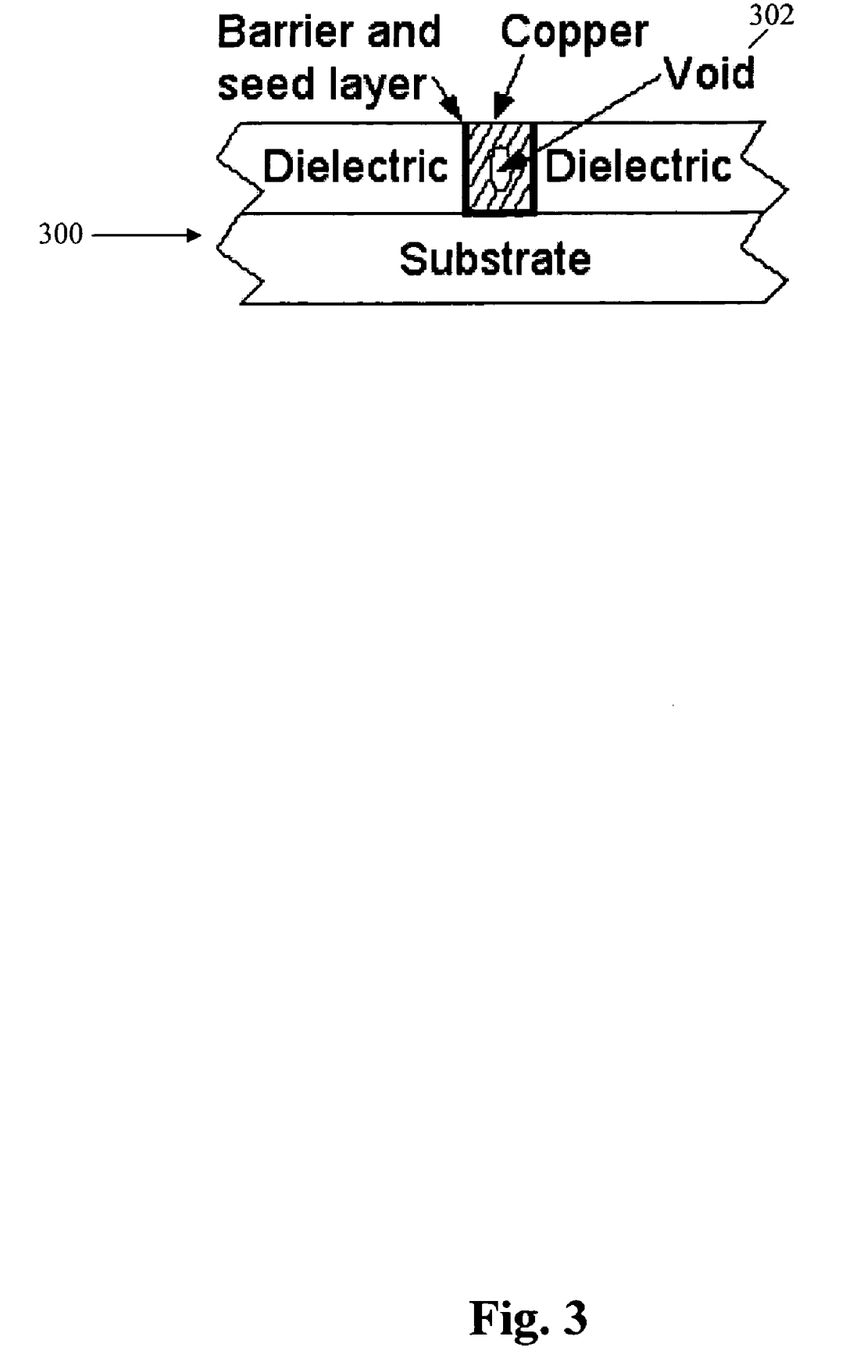
FIG. 3 schematically illustrates an example of a void defect in metal on an integrated circuit.
Figure 4:
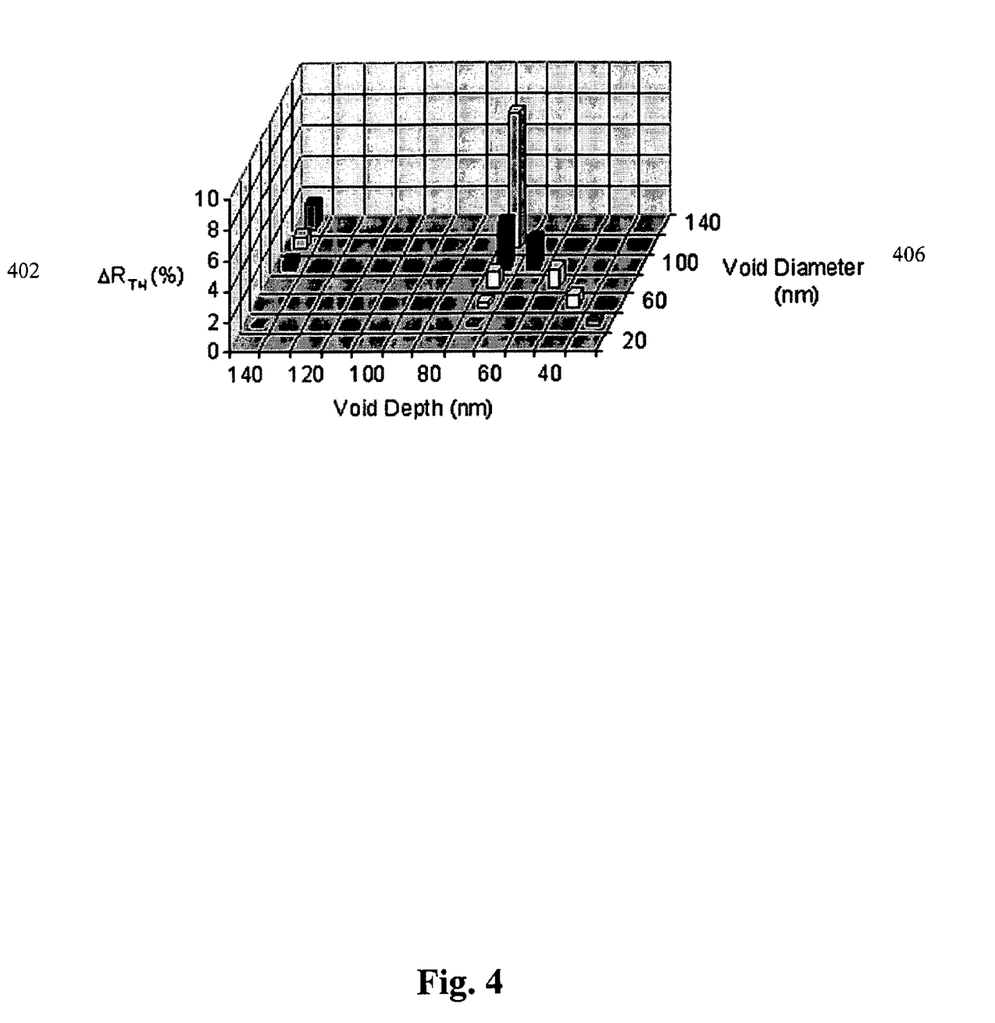
FIG. 4 presents an illustrative example of a change in thermal conductivity due to a void in copper interconnect.

(1) Detecting Voids in a Metal Interconnected on an Integrated Circuit Using Changes in Thermal Conductance Voids within an integrated circuit metallization layer are one type of defect that can be detected with the scanning thermal microscope. FIG. 3 schematically illustrates a structure of an integrated circuit 300 with a void 302 in the metal. Conventionally, during the manufacture of integrated circuits with copper interconnects, the copper is deposited using electroplating from the sidewalls of a trench. In the vicinity where the two copper surfaces meet, a seam is formed and very often voids are also formed due to irregularities in the manufacturing process. These voids affect the electrical performance and reliability of the integrated circuit, and merit detection as a consequence. The voids in the copper are typically filled with copper electroplating solution, which has a thermal conductance of approximately 1.6 W/mK, which is significantly lower than the thermal conductivity of copper, 400 W/mK. Thus, measuring the thermal conductance is an effective method of both locating the voids within copper, and obtaining information on the size of the voids. As a non-limiting, illustrative example, a simulated result of a structure whose dimensions are typical of those found in a 130 nm integrated circuit manufacturing process is shown in FIG. 4, where it is seen that the change in thermal conductance depends upon the void depth and size; this dependency allow defects in the integrated circuit to be classified by these parameters.

(2) Detecting Copper Voids from the Step Response

Figure 5:
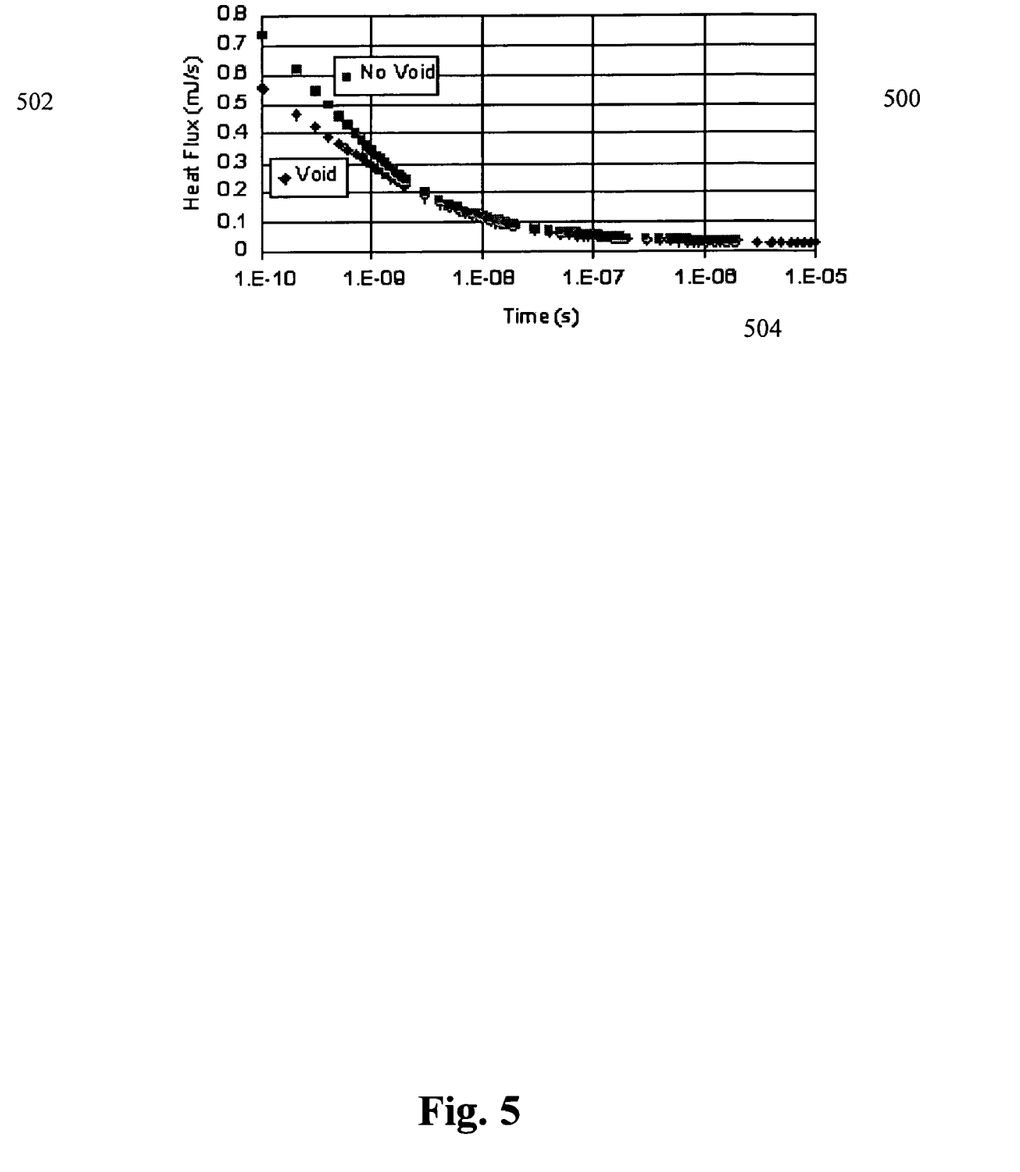
FIG. 5 illustrates an example of a time taken to heat a line of copper interconnect in an integrated circuit when a constant temperature is applied to the top surface of the integrated circuit.

Voids within copper may be found from the time-based thermal response 500. A temperature pulse (or other thermal stimulus) is applied to the copper structure and the heat flow 502 is measured as a function of time 504. The measured heat flow depends upon the thermal properties of the material in the vicinity of the thermal probe. A void in the copper will slow the thermal interaction between the probe and sample, as illustrated in FIG. 5. FIG. 5 shows a simulation of the difference in heat flow versus time for a solid copper line on an integrated circuit and for a copper line with a void in it; the example depicted in FIG. 5 is for illustrative purposes only, and is not intended in any way to limit the scope of the invention.

(3) Detecting Lattice Damage in a Semiconductor

A defect in a crystal lattice introduces a scattering site for phonons. The defects therefore affect the heat flux in semiconductors. Thus, damage in a semiconductor can be discerned by the changes in the thermal conductance. Ion implantation is a manufacturing technique that introduces significant crystalline damage to the silicon structure. By comparing the thermal conductivity of the sample with the thermal conductivity of a similar defect-free semiconductor, the degree of damage may be determined.

(4) Mapping Dopant Concentration in a Semiconductor

Ion implantation introduces dopant atoms to a semiconductor. The wafer is then annealed to significantly reduce the implant damage. The dopant atoms that are introduced to the silicon lattice introduce scattering sites for phonons, and thus decrease the thermal conductivity of a semiconductor. By comparing the thermal conductivity of the sample with the thermal conductivity of known dopant concentration, the dopant concentration may be determined.

(5) Measuring the Thickness of a Thin Film

By applying a periodic temperature waveform to the thermal probe tip, a thermal evanescent wave may be generated at the top surface of the sample. This evanescent wave propagates down through the sample, and any change in thermal diffusitivity will generate a reflected wave back towards the surface. In such a manner, constructive and destructive interference effects may be observed, analogous to the interference effects observed optically in thin films. This phenomenon can be used to find the thickness of thin films, whether they are transparent or opaque.

Figure 6A:
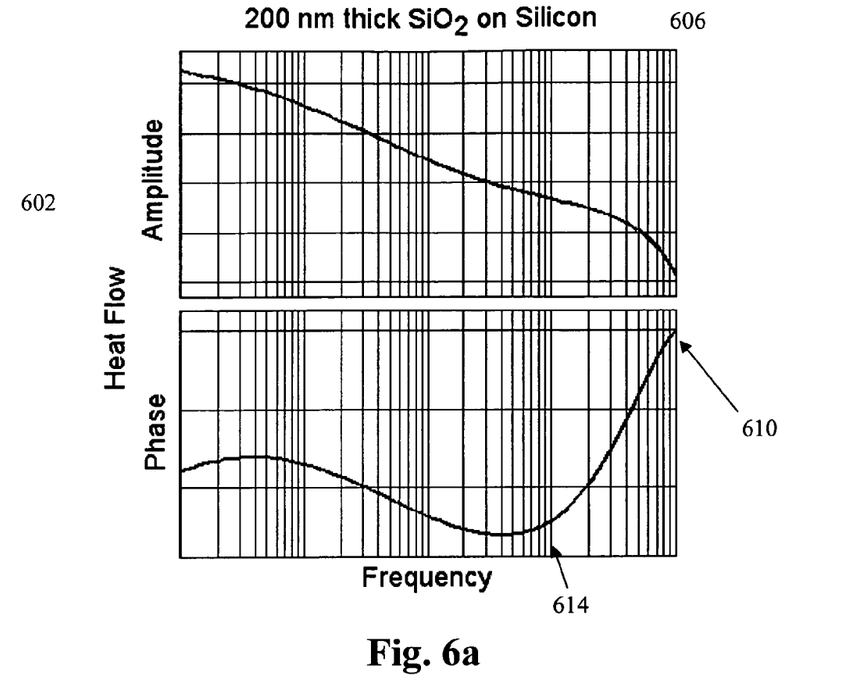
FIG. 6A-B illustrates examples of the magnitude and phase of heat flow from a thermal probe as a function of frequency for (A) 200 nm thick and (B) 1 nm thick silicon dioxide on a silicon substrate.
Figure 6B:
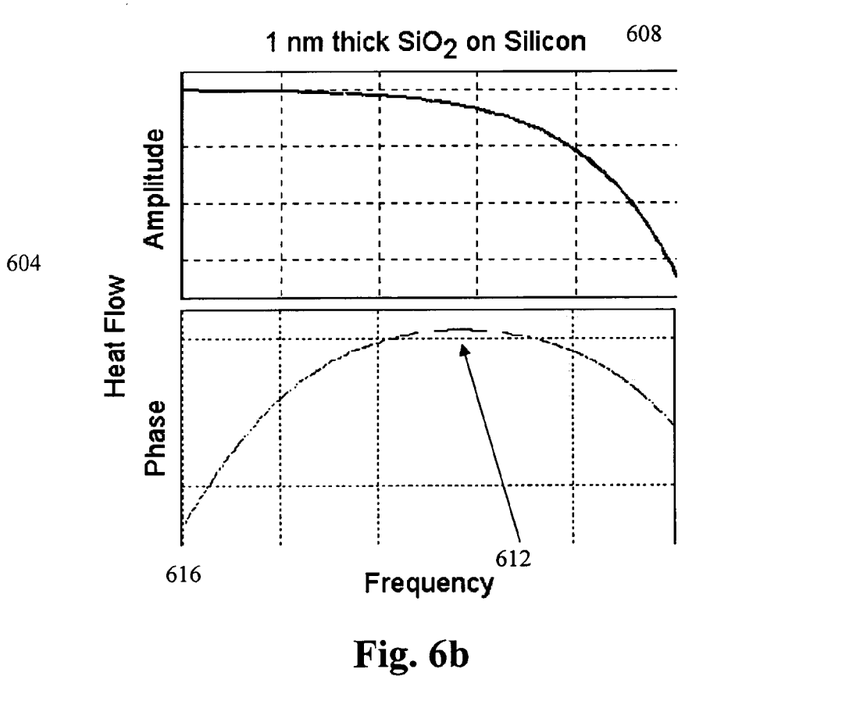

In other embodiments, the thickness of a thin film can be found from alternative techniques, including (1) a plot of the magnitude of heat flow versus frequency, and/or (2) from a plot of the phase of heat flow versus frequency. FIG. 6 illustrates a simulation result for a thin layer of silicon dioxide on top of a thick silicon substrate 604. As shown in the top plots of FIGS. 6A and 6B, the magnitude of heat flow 602 is distinctly different for the two thickness of silicon dioxide 606 608. As shown in the bottom plots of FIGS. 6A and 6B, the phase of heat flow is different for the two thicknesses, having maxima 610 612 and minima 614 616 at distinct frequencies that are thickness dependent.

Figure 7:
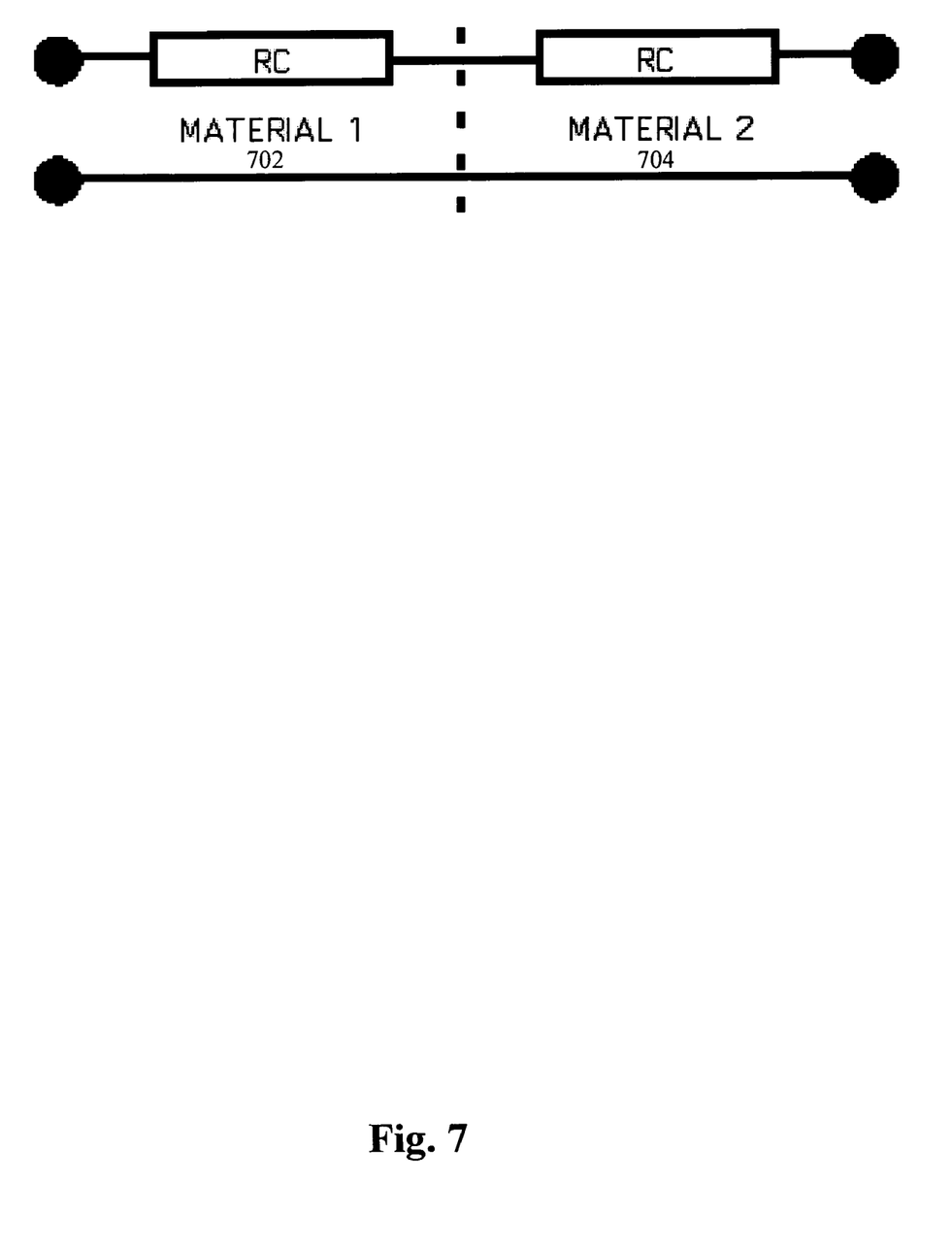
FIG. 7 illustrates an analogy between different layers of material and an electrical transmission line, in accordance with embodiments of the invention.

The path for heat flow is analogous to an electrical transmission line. In embodiments of the invention, the magnitude and phase of the heat flow are calculated analogously by using two or more electrical transmission lines in series, as shown in FIG. 7. Each material 702 704 is represented by a transmission line whose resistance and capacitance are calculated from the relatcor:

$$R = \frac{1}{\sigma_{th} A}$$

$$C = C_p \rho A$$

where $\sigma_{th}$ is the thermal conductivity of the material, A is the probe area, $C_p$ is the specific heat of the material, and $\rho$ is the density of the material. The length of each transmission line is the physical thickness of the layer.

(6) Temperature Mapping

Temperature mapping is performed by scanning a thermal probe across the sample surface and measuring the temperature at every location. This technique has several advantages over infrared (IR) imaging. First, it has a much higher spatial resolution, better than 50 nm, than can be achieved with IR. Second, calibration is easier because it is not necessary to know the material properties a priori, by contrast with IR.

Figure 8:
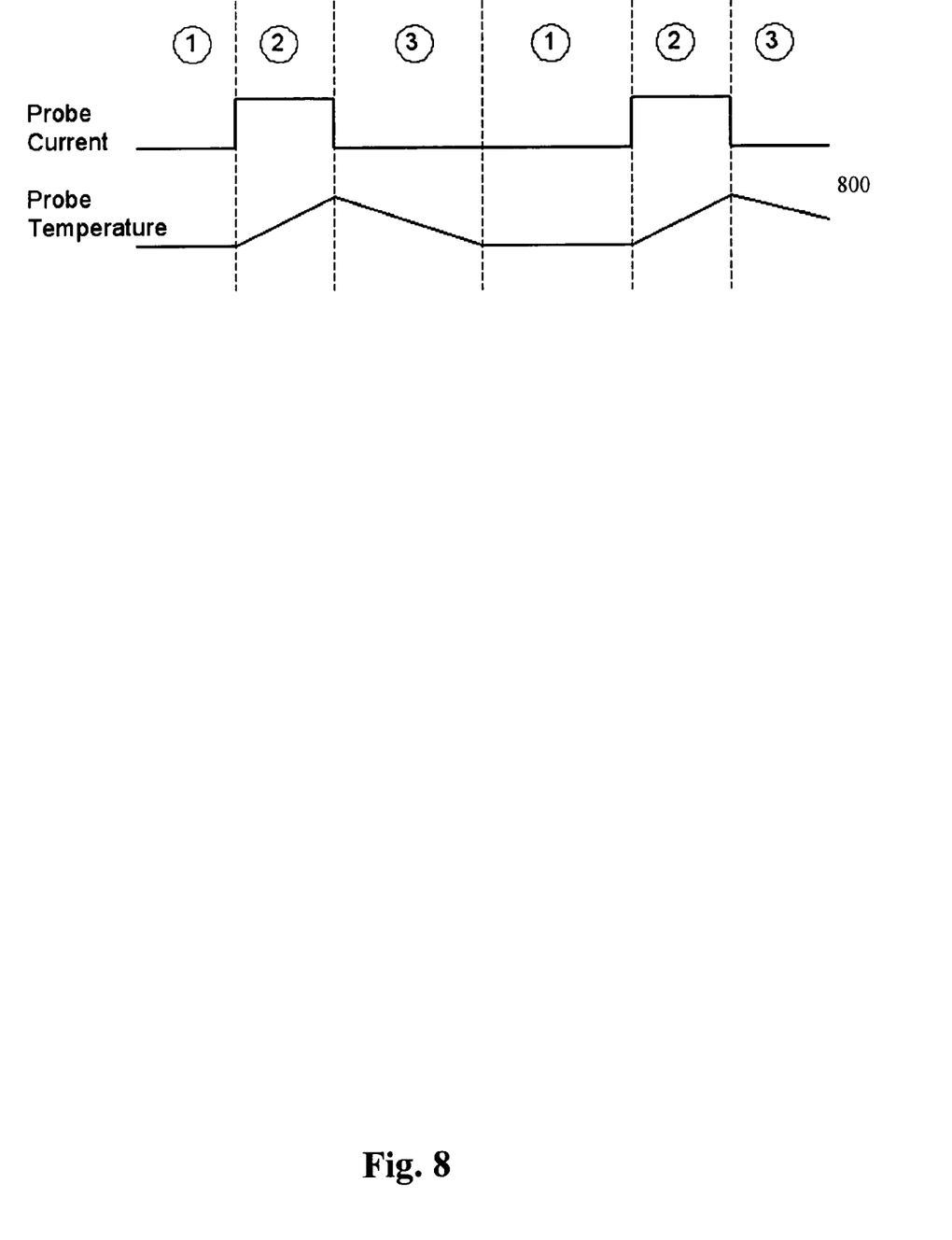
FIG. 8 illustrates a timing waveform for a method for reading the temperature of a bolometer thermal probe with a large current without significantly raising the probe temperature, in accordance with embodiments of the invention.

For a thermal probe with a bolometer as the sense element, embodiments of the invention perform temperature mapping by using a small current to prevent the temperature rise due to the current from significantly affecting the measurement. An alternative method used in embodiments of the invention measures the temperature using a bolometer by passing a large current through the bolometer for a very short period of time and measuring the voltage across the bolometer measured during this time. If the current pulse is significantly shorter in duration than the thermal time constant of the thermal probe, the temperature of the thermal probe will not appreciable increase and an accurate temperature may be measured. In some such embodiments, the measurement is not repeated until a period of time passes that is substantially as long as the thermal time constant of the thermal probe. This permits the thermal probe to achieve thermal equilibrium with the sample. A non-limiting, illustrative example of a waveform 800 demonstrating this procedure is given in FIG. 8. The temperature at each thermal probe in an array can be sequentially determined using the current pulse technique in a cost effective manner. In embodiments of the invention, a single circuit can be multiplexed to many thermal probes.

D. Conclusion

The foregoing disclosure of examples and embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A method of measuring properties of a film sample, comprising:

scanning across the sample one or more microstructures, the one or more microstructures containing at least one thermal probe and at least one of a thermal sensor and a thermal stimulator;

applying a stimulus to the one or more microstructures wherein the stimulus includes a temporally varying waveform;

detecting a response of the one or more microstructures from an interaction of the sample and the applied stimulus; and correlating a position of the one or more microstructures with the response of the one or more microstructures;

the response of the one or more microstructures is used to determine the thickness of barrier films deposited on an integrated circuit prior to a metal electroplating step on an integrated circuit.

2. The method of claim 1, wherein the temporally varying waveform includes a periodic component that has a frequency greater than $10^{-5}$ Hz.

3. The method of claim 1, further including:

storing the response of the one or more microstructures.

4. The method of claim 1, further including measuring a phase difference between the applied stimulus and the detected response.

5. The method of claim 4, further including identifying a maxima and a minima of the phase difference.

6. The method of claim 1, further including measuring an amplitude of the detected response.

7. The method of claim 1, wherein the response of the one or more microstructures includes an increase in temperature occurring in a time period shorter than a thermal time constant of the one or more thermal probes.

8. The method of claim 1, further including maintaining the one or more microstructures at a substantially constant temperature.

9. The method of claim 1, wherein the stimulus is applied for a duration of time substantially shorter than a thermal time constant of the one or more microstructures.

10. The method of claim 1, wherein the one or more microstructures includes a microbolometer in proximity to a tip of the one or more microstructures.

11. The method of claim 1, wherein the one or more microstructures includes a thermocouple in proximity to a tip of the one or more microstructures.

12. The method of claim 1, further including applying a light source in proximity to a tip of the one or more microstructures.

13. The method of claim 1, wherein the one or more microstructures is actuated with one of a motor actuator and linear actuator with a travel distance of 1 cm to 30 cm and a position accuracy of 1 micrometer to 5 nanometer.

14. The method of claim 1, wherein the stimulus heats the sample through a tip of the one or more thermal probes.

15. The method of claim 1, wherein the stimulus generates a thermal evanescent wave in the sample.

16. The method of claim 1, wherein the stimulus generates a thermal-acoustic wave in the sample.

17. The method of claim 1, wherein the response of the one or more microstructures is used to identify defects within said sample.

18. The method of claim 1, wherein the sample is an integrated circuit.

19. The method of claim 18, wherein the response of the one or more microstructures is used to identify voids in the metal layers of the integrated circuit.

20. The method of claim 18, wherein the response of the one or more microstructures is used to identify a partially or fully blocked contact between metal layers on the integrated circuit.

21. The method of claim 18, wherein the response of the one or more microstructures identifies crystalline damage due to ion implantation in the integrated circuit.

22. The method of claim 1, wherein the sample is a semiconductor, and the response of the one or more microstructures identifies crystalline defects the in semiconductor.

23. The method of claim 1, further comprising: mapping a concentration of dopant atoms in the sample at a submicron resolution.

24. The method of claim 1, further comprising: measuring one or more grain boundaries in the sample, wherein the sample includes polycrystalline materials.

25. The method of claim 1, wherein the response of the one or more microstructures identifies cracks within a layer of the sample.

26. The method of claim 1, wherein the response of the one or more thermal probes identifies a presence of a boundary between two dissimilar materials contained in the sample, and the response further identifies one or more characteristics of the boundary, the one or more characteristics selected from the group consisting of: a strength of the boundary, a uniformity of the boundary, and a uniformity of a bond between the dissimilar materials.

27. The method of claim 26, wherein the stimulus includes an evanescent wave and the response of the one or more thermal probes includes thermal wave interference from the two dissimilar materials.

28. The method of claim 1, wherein the response of the one or more microstructures identifies a thickness of the sample, wherein the sample comprises a thin film.

29. The method of claim 28, where the response of the one or more microstructures is used to identify the thickness of metal on an integrated circuit.

30. The method of claim 28, where the response of the one or more microstructures is used to identify the thickness of dielectric films on an integrated circuit.

31. The method of claim 1, where the response of the one or more microstructures is used to determine the localized temperature of the sample.

32. A method of measuring properties of a film sample, comprising:
   scanning across the sample one or more microstructures, the one or more microstructures containing at least one thermal probe and at least one of a thermal sensor and a thermal stimulator;
   applying a stimulus to the one or more microstructures wherein the stimulus includes a temporally varying waveform;
   detecting a response of the one or more microstructures from an interaction of the sample and the applied stimulus;
   correlating a position of the one or more microstructures with the response of the one or more microstructures;
   the response of the one or more microstructures identifies a thickness of the sample, and wherein the sample comprises a thin film; and
   the response of the one or more microstructures is used to determine the thickness of barrier films deposited on an integrated circuit prior to a metal electroplating step on an integrated circuit.

33. A method of measuring properties of a film sample, comprising:
   scanning across the sample one or more microstructures, the one or more microstructures containing at least one thermal probe and at least one of a thermal sensor and a thermal stimulator;
   applying a stimulus to the one or more microstructures wherein the stimulus includes a temporally varying waveform;
   detecting a response of the one or more microstructures from an interaction of the sample and the applied stimulus;
   correlating a position of the one or more microstructures with the response of the one or more microstructures; and
   wherein the one or more microstructures is used to determine the thickness of the barrier films deposited on an integrated circuit prior to a metal electroplating step on an integrated circuit.

34. A method of measuring properties of a sample, comprising:
   scanning across the sample one or more microstructures, the one or more microstructures containing at least one thermal probe including at least one of a thermal sensor and a thermal stimulator;
   applying a conductive heat stimulus to the one or more microstructures wherein the stimulus includes a temporally varying waveform;
   detecting a conductive heat response of the one or more microstructures from an interaction of the sample and the applied stimulus; and
   correlating a position of the one or more microstructures with the response of the one or more microstructures.

* * * * *